United States Patent
Aalders

(10) Patent No.: US 8,750,952 B2
(45) Date of Patent: Jun. 10, 2014

(54) APPARATUS AND METHOD FOR DATING A BODY SAMPLE

(75) Inventor: Maurice Christian Gerard Aalders, Amsterdam (NL)

(73) Assignee: Academisch Medisch Centrum (NL)

( * ) Notice: Subject to any disclaimer, the term of this patent is extended or adjusted under 35 U.S.C. 154(b) by 689 days.

(21) Appl. No.: 12/988,725

(22) PCT Filed: Apr. 21, 2009

(86) PCT No.: PCT/IB2009/005331
§ 371 (c)(1),
(2), (4) Date: Jan. 14, 2011

(87) PCT Pub. No.: WO2009/130580
PCT Pub. Date: Oct. 29, 2009

(65) Prior Publication Data
US 2011/0112385 A1 May 12, 2011

(30) Foreign Application Priority Data

Apr. 21, 2008 (GB) .................................. 0807265.4
Apr. 20, 2009 (GB) .................................. 0906759.6

(51) Int. Cl.
*A61B 5/1455* (2006.01)
(52) U.S. Cl.
USPC ............................ 600/310; 600/322; 600/476
(58) Field of Classification Search
USPC .......... 600/310, 322, 323, 324, 326, 473, 476
See application file for complete search history.

(56) References Cited

FOREIGN PATENT DOCUMENTS

| DE | 19638839 | 3/1998 |
| DE | 19811142 | 9/1999 |
| WO | WO2006117526 | 11/2006 |

OTHER PUBLICATIONS

Klein A et al., "Estimating the age of hematomas in living subjects based on spectrometric measurements," The Wound Healing Process: Forensic Pathological Aspects (Oehmichen and Kirchner, eds), Schmidt-Romhild, pp. 283-291, 1995.*
Randeberg, LL et al., "A novel approach to age determination of traumatic injuries by reflectance spectroscopy," Lasers in Surgery and Medicine, vol. 38, pp. 277-289, 2006.*

* cited by examiner

*Primary Examiner* — Eric Winakur
(74) *Attorney, Agent, or Firm* — Hartman Global IP Law; Gary M. Hartman; Domenica N.S. Hartman

(57) ABSTRACT

A method and apparatus for dating a body sample, for example a sample of body fluid involves taking a series of spectroscopic measurements of the sample, each measurement in the series including at least two predetermined positions in the spectrum. The positions have spectral characteristics corresponding to two or more predetermined substances present in the sample that have a time varying relationship with each other. The measurements in the series are spaced in time. A concentration of each of the substances present in the sample is then determined from each of the spectroscopic measurements at each point in time. Next, a ratio of the concentrations of the two predetermined substances at each point in time is determined and then the ratios of the concentrations of the two predetermined substances over time are analyzed to estimate when the concentrations of the two substances were at a limit of their concentrations, thereby providing an indication of the age of the sample. The sample may be blood, which may be either within the body (e.g. as a bruise), or external to the body.

11 Claims, 16 Drawing Sheets

APPARATUS AND METHOD FOR DATING A BODY SAMPLE

CROSS REFERENCE TO RELATED APPLICATIONS

This application claims the benefit of International Application No. PCT/IB2009/005331 filed Apr. 21, 2009, having a claim of priority to GB patent application number 08 07265.4, filed Apr. 21, 2008, and GB patent application number 09 06759.6, filed Apr. 20, 2009.

The present invention relates to an apparatus and method for dating a body sample, preferably, but not exclusively, a sample of body fluid, such as blood, which may be external to the body, for example, having caused stains on an external substrate, such as a floor, wall, etc., or which may be within a body, thereby showing as bruising, or a body sample, such as skin.

It is well known that dating of both external blood stains and internal bruising is a useful forensic technique to determine when a particular injury was caused to a person. In the one case, the injury would have been such that the skin was punctured and blood was spilt and in the other case no blood was spilt externally, but bruising, to a greater or lesser extent was caused. In both cases, however, there is a need to accurately determine the age of the injury.

In general, determination of the age of external blood stains has been carried out by a variety of methods. Although, historically, this was carried out by very roughly estimating the age based on the colour of the blood stain, more "scientific" methods have recently been employed. Most such methods rely on the fact that, when blood leaves the human body, haemoglobin in the blood is oxidised to met-haemoglobin. Various methods have therefore tried to use different characteristics of haemoglobin and met-haemoglobin to try to determine their relative concentrations and, from those, to try to determine the age of the blood stain. However, some of these methods require very complicated and advanced technical equipment, so that they cannot easily be done at the scene of the injury, for example a crime scene. In other cases, known techniques often compromise the bloodtraces by using chemicals or by requiring that the stains be taken to a laboratory in order to properly analyse them. Still others of the methods have proved not to be reliable since they provide too high a deviation compared to the actual age of the stains. One recent new technique that has been suggested is to use atomic force microscopy for high-resolution imaging of erythrocytes in a blood sample to detect elasticity changes on a nanometer scale (see the paper "Age determination of blood spots in forensic medicine by force spectroscopy" by Stefan Strasser, Albert Zink, Gerald Kada, Peter Hinterdorfer, Oliver Peschel, Wolfgang M. Heckl, Andreas G. Nerlich and Stefan Thalhammer published in Forensic Science International, Volume 170, Issue 1, 20 Jul. 2007, Pages 8-14).

More recently, there has also been a greater impetus to be able to accurately date bruises, particularly since cases of child abuse appear, unfortunately, to be more common, often exhibiting bruising. Furthermore, in some such cases, there may be several overlapping bruises of different ages. To date, in general, the age of particular bruises has been estimated by comparing their colour with a chart. Although such charts have been used for many years, they have only recently been studied for accuracy and it has been found that the estimates so produced can be substantially inaccurate because bruises do not exhibit changing colour in different people at the same rate or to the same extent for a number of reasons, including, for example, the age of the person, the person's skin colour, the depth of the bruise, diseases and drugs that person may have, and even the amount of previous bruising the person has experienced.

Bruising occurs when mechanical force is applied to a person's (for example, a child's) skin to such a degree that capillaries (and potentially also larger vessels) disrupt, resulting in the leakage of blood into the subcutaneous, tissue and then into the dermal layer. The amount of blood, the size and location of the involved area and the time after inflicting the injury account for the appearance (colour) of the bruise (haematoma). Discrepancies between physical findings and the history given by carers are hallmarks of child abuse. Another factor coupled to child abuse is the observation of several bruises at different stages of healing on the victim's body. Apart from for recognizing abuse, ageing is also important to identify the perpetrator(s) and to determine whether multiple episodes of trauma occurred. In general, a bruise progresses through a series of colours beginning with deep red, blue, or purple, then changes to a deep blue, then greenish, and, finally, resolves with a yellowish brown colour. The various colours emanate from the breakdown of the extravasated blood into the components of haemoglobin (e.g., through biliverdin, bilirubin). However, despite the widespread use, determining the bruise's age by its colour is still a subjective step that does not take into account the individual patient's circumstances, such as skin colour and the various other variables mentioned above, including the bruise's location (whether overlying soft tissue or bone).

It has therefore been considered that accurate colorimetry may be able to determine the colour of the bruise more subjectively and therefore provide better estimates. However, such techniques still do not take into account the individual person's circumstances. At best, they provide a more accurate measure of the actual colour of the bruise at the time the measurement is taken. Nevertheless, even these techniques do not guarantee an accurate enough reading of colour Optical reflectance spectroscopy is one solution for this problem. Various papers have described such techniques; for example "Spectrophotometric and tristimulus analysis of the colors of subcutaneous bleeding in living persons" by Yukihito Yajima, Masato Funayama (published in Legal Medicine, Volume 5, Pages S342-S343 * Supplement 1, March 2003, Pages S342-S343) and "The practical application of reflectance spectrophotometry for the demonstration of haemoglobin and its degradation in bruises" by V K Hughes, P S Ellis, T Burt and N E I Langlois published in J. Clin. Pathol. 2004; 57; 355-359. More recently, serial spectroscopic point measurements of bruises showed a time dependent change in the spectra which was attributed to the amount of bilirubin in the skin (see the paper "Optical Classification of Bruises" by L. L. Randeberg, A. Winnem, S. Blindheim, O. A. Haugen, L. O. Svaasand, published in Proceedings of SPIE, 5312, 54-64, 2004. This group developed a mathematical model for the diffusion of blood in the tissue and the conversion to bilirubin. The model predicts the age of a haematoma with an accuracy of approximately 1 day. Nevertheless, there are several unknown variables in the model, i.e. the various relaxation times, the dermal thickness, and spatial information.

According to a first aspect of the present invention, there is provided a method of dating a body sample comprising taking a series of spectroscopic measurements of the sample, each measurement in the series including at least two predetermined positions in the spectrum, the positions having spectral characteristics corresponding to at least two predetermined substances present in the sample that have a time varying relationship with each other, the measurements in the series being spaced in time, determining a concentration of each of the substances present in the sample from each of the spectroscopic measurements at each point in time, determining a ratio of the concentrations of the two predetermined substances at each point in time, analysing the ratios of the concentrations of the two predetermined substances over time to estimate when the concentrations of the two substances were at a limit of their concentrations, thereby providing an indication of the age of the sample.

In one embodiment, the sample is outside the body, and may be, for example, skin, or may be a fluid, such as blood. One of the two predetermined substances may be haemoglobin and the other substance may be met-haemoglobin.

In another embodiment, the sample is inside the body, and may be, for example, a fluid, such as blood. One of the two predetermined substances may be haemoglobin and the other substance may be bilirubin.

The spectroscopic measurements may comprise reflectance, Raman or fluorescence spectroscopic measurements.

The spectroscopic measurements may comprise interferometric spectroscopic measurements whereby the measurements are made at a series of depths in the body.

The spectroscopic measurements may include measurements made at several different lateral positions on the body.

The spectroscopic measurements may provide several series of measurements, for each of which an estimate of when the concentrations of the two substances were at a limit of their concentrations is determined, and the estimates for all the series are analysed provide an indication of the age of the sample.

Several embodiments of the invention will now be described, by way of example only, with reference to the accompanying drawings, in which.

Figure 1:
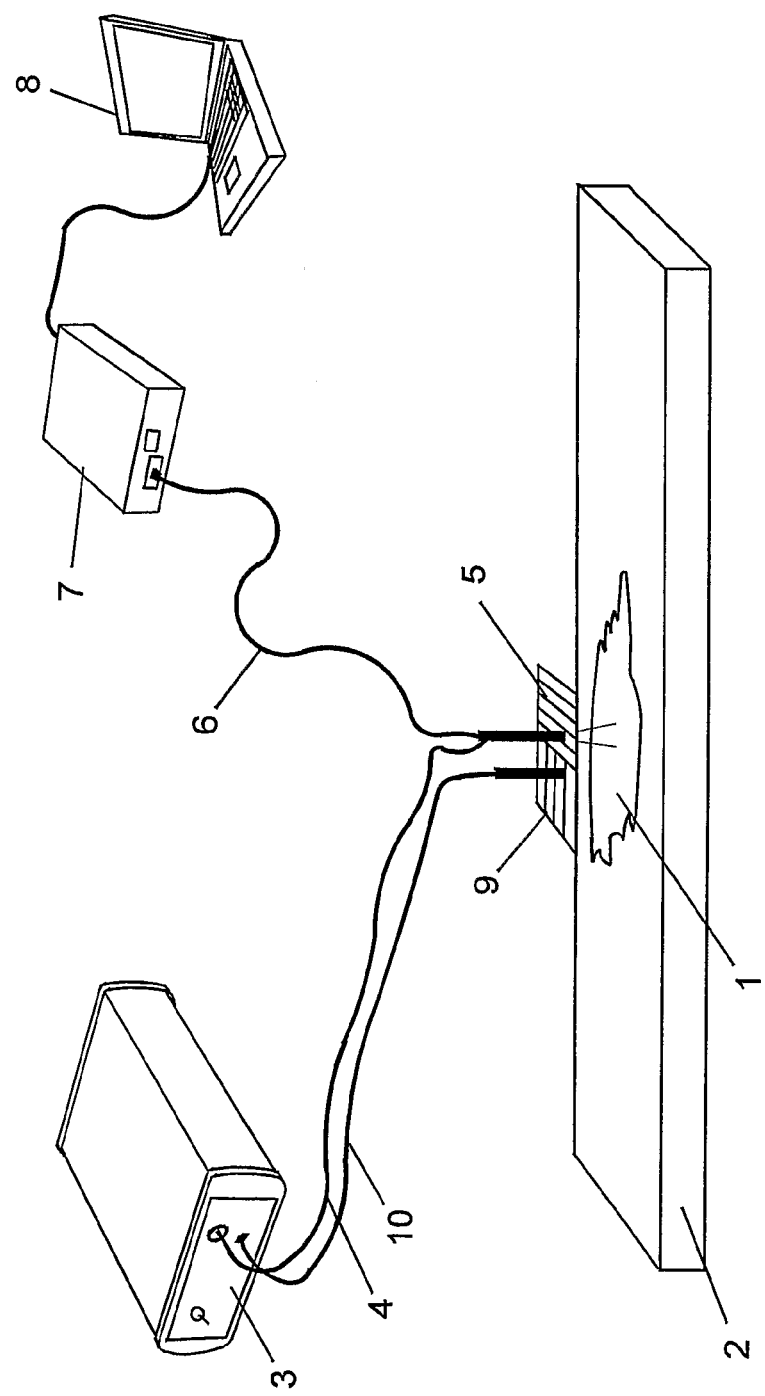
FIG. 1 is a schematic diagram of an apparatus constituting a first embodiment of the invention.

Referring first to FIG. 1, there is shown a schematic apparatus for measuring the age of bloodstains on a substrate. As shown, the bloodstain 1 is present on a host material 2. The bloodstain 1 is illuminated by light from a light source 3 via a first optical fibre 4. The light is directed onto the bloodstain from the end of the first optical fibre 4 via a linear polarizer 5. A second optical fibre 6 is arranged next to first optical fibre 4 to detect light that is reflected from the bloodstain 1 and which passes back through the linear polarizer 5. Such reflected light is, of course, low-order scattered, since its polarization has not been substantially changed. This low-order scattered reflected light is then transmitted via the second optical fibre 6 to a spectrograph 7. The results of the spectrograph, which will be further explained below, are then passed to a computer 8 for processing. A cross polarizer 9 is provided next to the linear polarizer and a third optical fibre 10 is arranged to detect light reflected from the bloodstain 1 that passes through the cross polarizer. This reflected light will be high-order scattered light and this light is transferred via the third optical fibre 10 to a second channel of the spectrograph. This light will contain information of the host material, later to be used for correction. Low-order scattered light comes from the top of the blood and high-order from the bottom (or from the host material).

Figure 2:
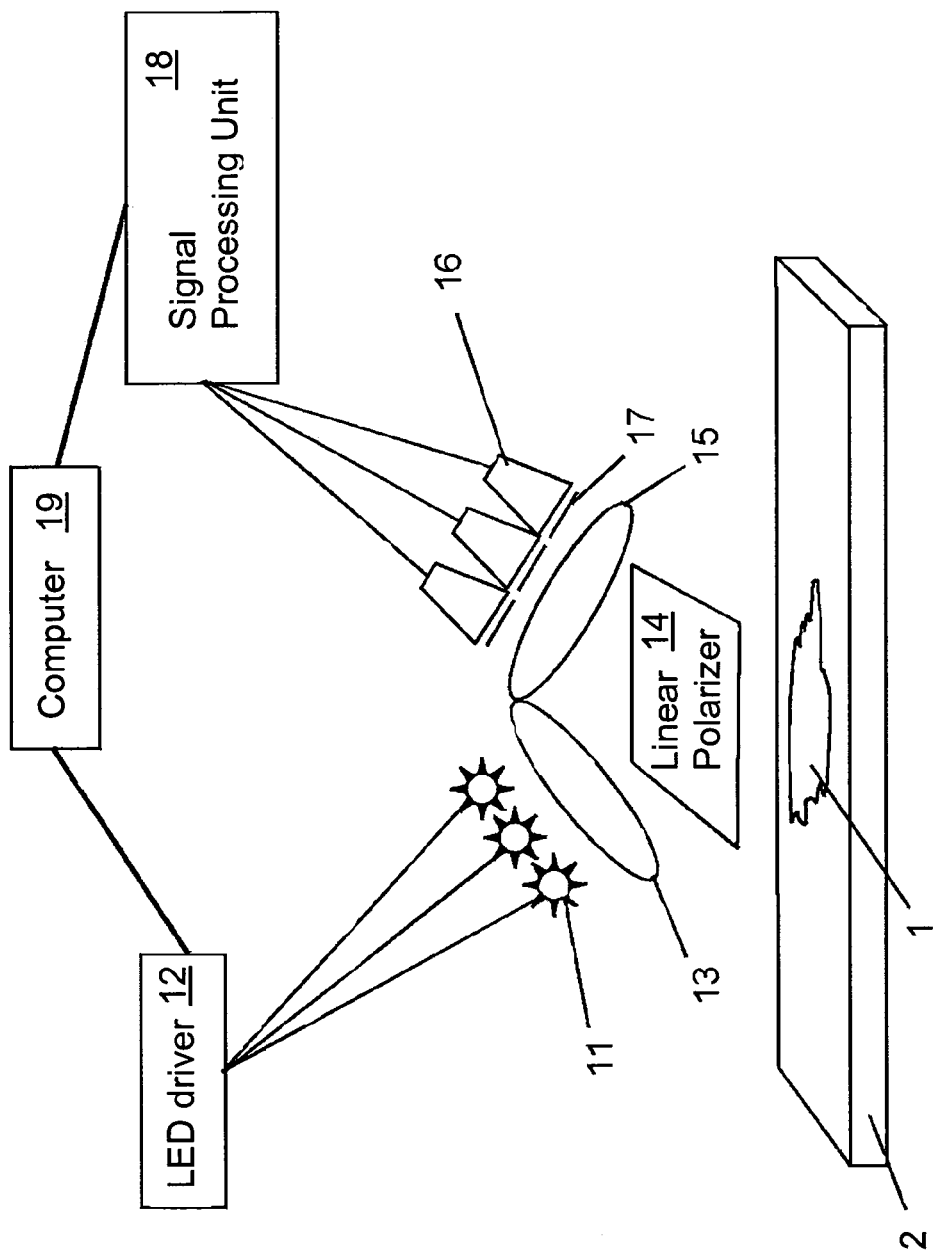
FIG. 2 is a schematic diagram of an apparatus constituting a second embodiment of the invention.

FIG. 2 shows a second embodiment of similar apparatus to that of FIG. 1, but with different forms of the same basic elements. Thus, in this case, the bloodstain 1 is again on the host material 2, but this time it is illuminated by light produced by several Light Emitting Diodes (LEDs) 11 controlled and driven from an LED driver 12. The LEDs 11 are different, so that each emits light of a different wavelength or waveband from that of the other LEDs 11. The light from the LEDs 11 illuminates the bloodstain 1 via a first lens 13 and a linear polarizer 14. In this case, a second lens 15 directs the light reflected from the bloodstain and transmitted back through the linear polarizer 14, i.e. the low-scattered light, to several photo detectors 16, each of which has a different filter 17 between it and the second lens 15, so that each photodetector 16 detects reflected light of a different wavelength or waveband from that of the other photodetectors 16. The filters 17 are matched to transmit light of the wavelengths or wavebands that are emitted by the LEDs 11. The outputs from the photodetectors 16 are passed to a signal processing unit 18, which is coupled to a computer 19. The computer 19 is also used to control the LED driver 12. This implementation can be easily designed into a hand held measurement device, to enable ease of use at, for example, a crime scene. Again, low-order scattered light comes from the top of the blood. As explained below with reference to FIG. 4, haemoglobin has an absorption peak at 556 nm, oxy-haemoglobin has a pair of peaks at 542 and 578 nm, and met-haemoglobin has a peak at 630 nm. The isosbestic points for haemoglobin and oxy-haemoglobin (where their absorptions are equal) occur at 549, 569, and 586 nm. Accordingly, it is preferable that the LEDs emit at these wavelengths, i.e. at 542, 556, 578, 630, 569 nm.

Figure 3:
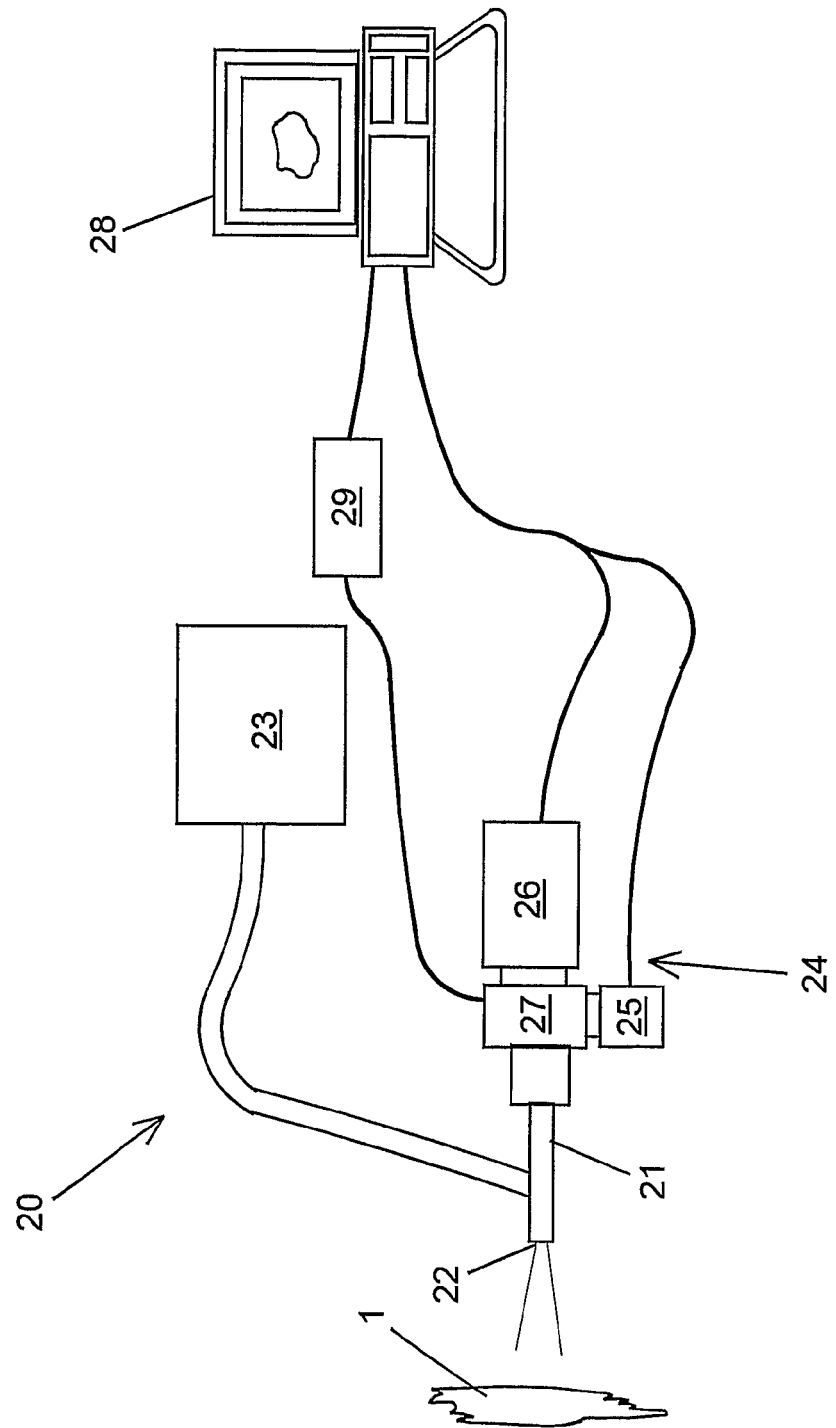
FIG. 3 is a schematic diagram of an apparatus constituting a third embodiment of the invention.

FIG. 3 shows a third embodiment of the apparatus. In this case, the bloodstain 1 is illustrated as being in a vertical plane, for example on a wall. In this case, a hand-held apparatus 20 includes a light guide 21 having an appropriate optical system at an end 22 thereof for transmitting illuminating light from an input light module 23 through the optical system and out onto the bloodstain. Reflected light is then detected through the optical system and transmitted through the light guide 21 to a Spectral Imaging Camera 24. The Spectral Imaging Camera 24 includes both a colour camera 25 and an intensified camera 26. The detected light from the bloodstain 1 transmitted through the light guide 21 passes through an Acousto-Optic Tunable Filter (AOTF) 27 from where it is directed to either the colour camera 25 or the intensified camera 26 (or both). The AOTF operates as a tunable band pass filter, the centre wavelength of which can be rapidly tuned across a wide spectral range by changing the frequency of an applied radio frequency (RF) signal. The Spectral Imaging Camera 24 is coupled to a computer 28, which both receives the output data from the Spectral Imaging Camera 24 for analysis and controls the Spectral Imaging Camera 24, including the colour camera 25, the intensified camera 26, and the AOTF 27 via AOTF control electronics 29. Advantages of the AOTF, apart from electronic tuning, include a large angular aperture, high spectral resolution, fast response time and variable filtering efficiency. Any filtering wavelength in the range from 400 to 800 nm can be rapidly selected either by random access or sequential tuning which, in the last case, yields a full reflection spectrum for every pixel on the CCD (=every position on the tissue). In addition, both filtered (spectral) and unfiltered (white light) images are available to facilitate the direct association of spectroscopic features with specific anatomical sites.

The most direct mode of spectral imaging is to illuminate the target area while acquiring a series of images assessing the remittance spectrum of every pixel. This data set is called a 'spectral cube', containing information about the absorbers in the tissue which allows determining relative concentrations of the absorbers. One such AOTF is manufactured by Gooch and Housego (UK) and has an active aperture of 6×6 mm$^2$, a tuning range from 480 to 700 nm (which means that a separate detector is required for measuring water absorption), a diffraction efficiency of approximately 95% at 632 nm and a filtering bandwidth of nominally 5.7 nm (collimated light).

However, it will be appreciated that other filters can be used depending on the application and the accuracy of the results required. Thus, for example, a liquid crystal tuneable filter, which is simpler to use and easier to design could be used instead of the AOTF. In any event, both types of filter produce data in the form of a spectral cube, which contains information about the absorbers in the tissue which can be used to determine relative concentrations of the chromophores. The reflected light at each position will be used to calculate the corresponding absorption spectrum at each pixel or group of pixels. This will provide the position dependent concentrations of the chromophores.

Figure 4:
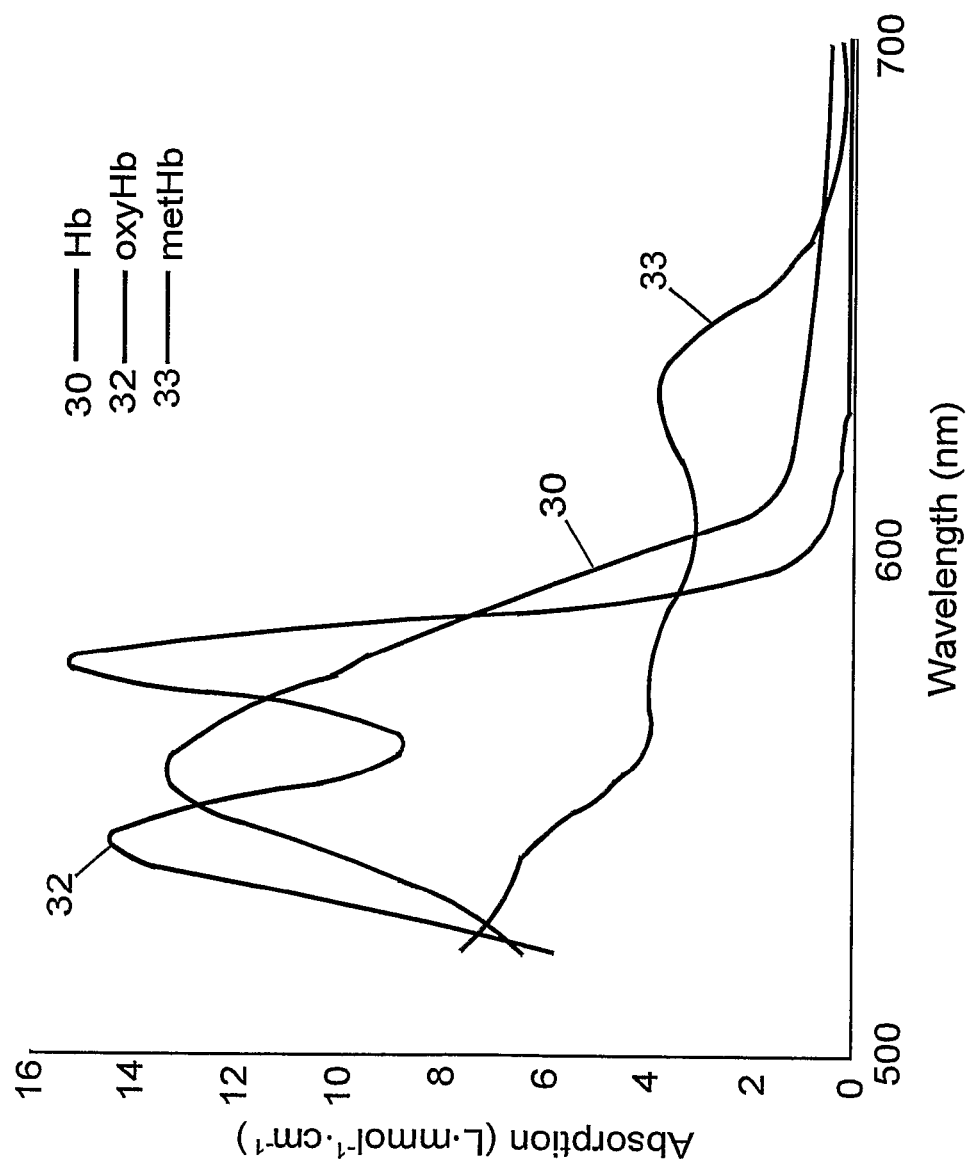
FIG. 4 shows absorption spectra for haemoglobin, met-haemoglobin and oxy-haemoglobin.

FIG. 4 shows absorption spectra for haemoglobin (30), met-haemoglobin (31) and oxy-haemoglobin (32). It will be seen that haemoglobin has an absorption peak at 556 nm, wry-haemoglobin has a pair of peaks at 542 and 578 nm, and met-haemoglobin has a peak at 630 nm. The isosbestic points for haemoglobin and wry-haemoglobin (where their absorptions are equal) occur at 549, 569, and 586 nm. Given these known spectra, as well as for water, measuring the levels of met-haemoglobin and oxy-haemoglobin and comparing their ratio over time with a model of the rate at which oxy-haemoglobin is converted to met-haemoglobin allows an accurate estimate of the time since that conversion stated, i.e. when the blood was first spilt.

It will thus be seen that by using that by measuring the detected light, one can determine the (relative) quantities of the contents of the measured volume. From the total reflectance spectrum for the bloodstain, for the host material, for example coloured cloth, and a reference spectrum for the light source, one can correct for the properties of the light source and obtain the corrected reflectance of the bloodstain. From these spectra, the relative concentrations of the chosen substances in the bloodstain can be determined. By carrying out these measurements over time, we can determine how those relative concentrations vary over time.

Figure 5:
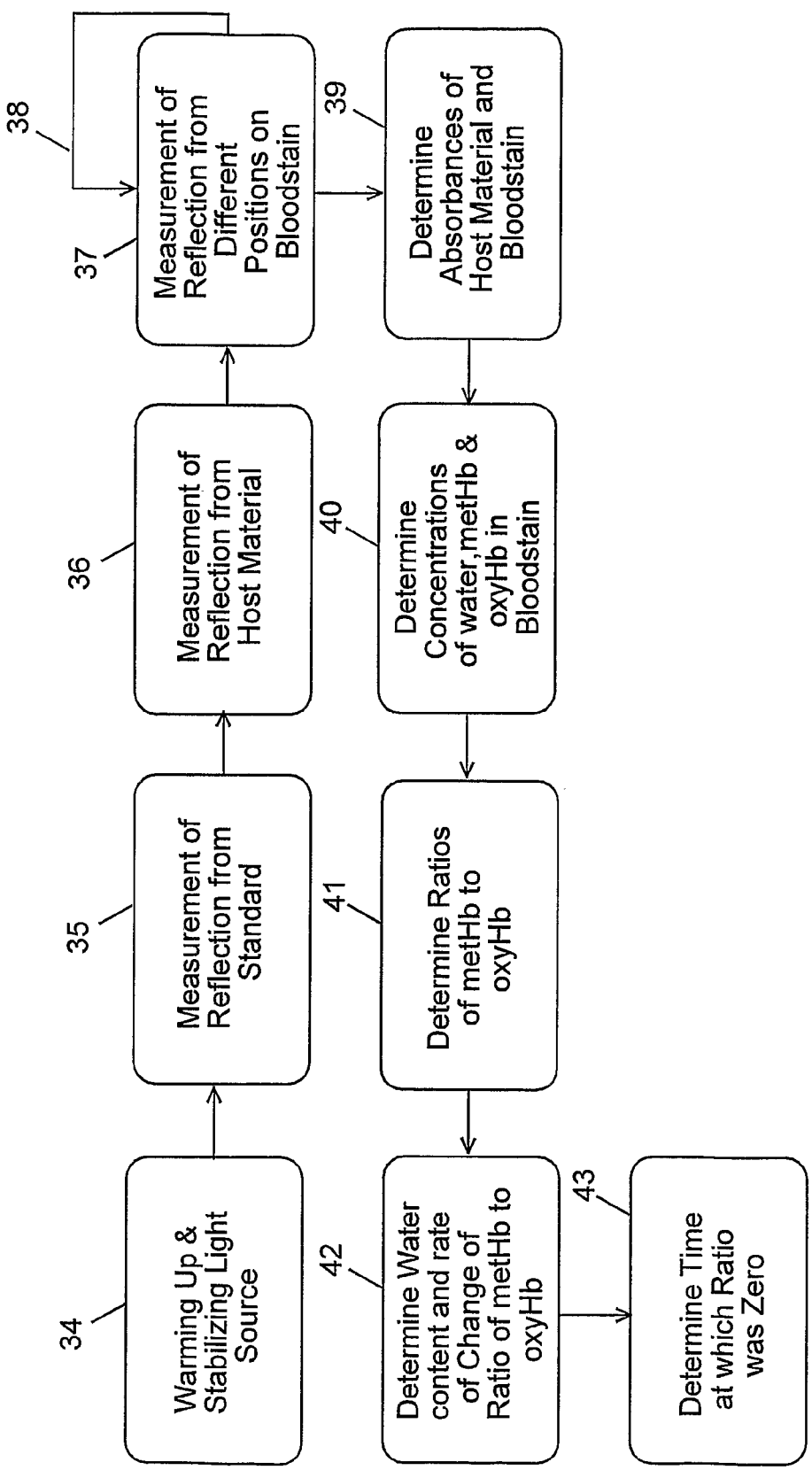
FIG. 5 is a schematic flowchart of the process for determining the time at which blood was first exposed to air.

Thus, the process of determining the relative quantities of oxy-haemoglobin, met-haemoglobin and water in order to calculate the moment of deposition of extracorporeal blood is based on a spectroscopic measurement technique which only measures the low order scattered light and fits the resulting data using a procedure that allows for the elimination of background artefacts and scaling of the absorption curves. The process is shown generally in FIG. 5.

As can be seen, the process starts by warming up and stabilising the light source 34. The time at which a stable output is reached depends on the type of light source. A halogen lamp requires 10-30 minutes, but LEDs can be used much sooner, although they have to be kept at a constant temperature. Once the light source is stabilised, in order to be able to correct for the spectrum of the particular light source being used, a reference spectrum is measured (35) using a neutral reflector, such as a spectralon. In this case, the light from the light source is made incident onto the spectralon and the reflected light is passed to the detector using the same light path, for example optical fibres if they are being used, so that a spectrum including the light source, the light paths and the detector characteristics can be obtained as a reference. Next, the reflection spectrum from the host material is obtained (36). Clearly, this will bear the characteristics of the reference spectrum plus the absorption and reflection characteristics of the host material. After these two references are obtained, measurement on the bloodstain is commenced. In this case, reflectance spectra are measured at different positions on the bloodstain (37). These same measurements at the same positions on the bloodstain are then repeated several or many times over the course of minutes, hours or even days, as is indicated by the arrow 38. The measurements have to be repeated in order to be able to be able to determine the reaction rate from which the initial time when the reaction started, i.e. when the blood was first exposed to the air, can be determined.

In essence, the absorbance of the host material and of the bloodstain can be found from:

$$\text{Absorbance hostmaterial} = \ln\left(\frac{\text{refl. hostmaterial}}{\text{refl. reference}}\right)$$

$$\text{Absorbance bloodstain} = \ln\left(\frac{\text{refl. bloodstain}}{\text{refl. reference}}\right)$$

From the measurements of the spectra, the absorbances of the host material and the bloodstain can be calculated (39).

The above relationships can be determined from a consideration of the simple mathematics of the spectra. Thus, for the host material, for example a piece of white cloth, the light detected is dependent on the incident light and on the absorbance of the material as follows:

$$I_{host} = I_0 e^{-\mu_{a,host}(\lambda) \cdot d_{host}}$$

where:
$I_{host}$ is the intensity of the detected light;
$I_0$ is the intensity of the incident light;

$\mu_{a,host}(\lambda)$ is the absorption coefficient of the host material (in mm$^{-1}$) at wavelength $\lambda$; and $d_{host}$ is the optical pathlength through the host (in mm).

Figure 6:
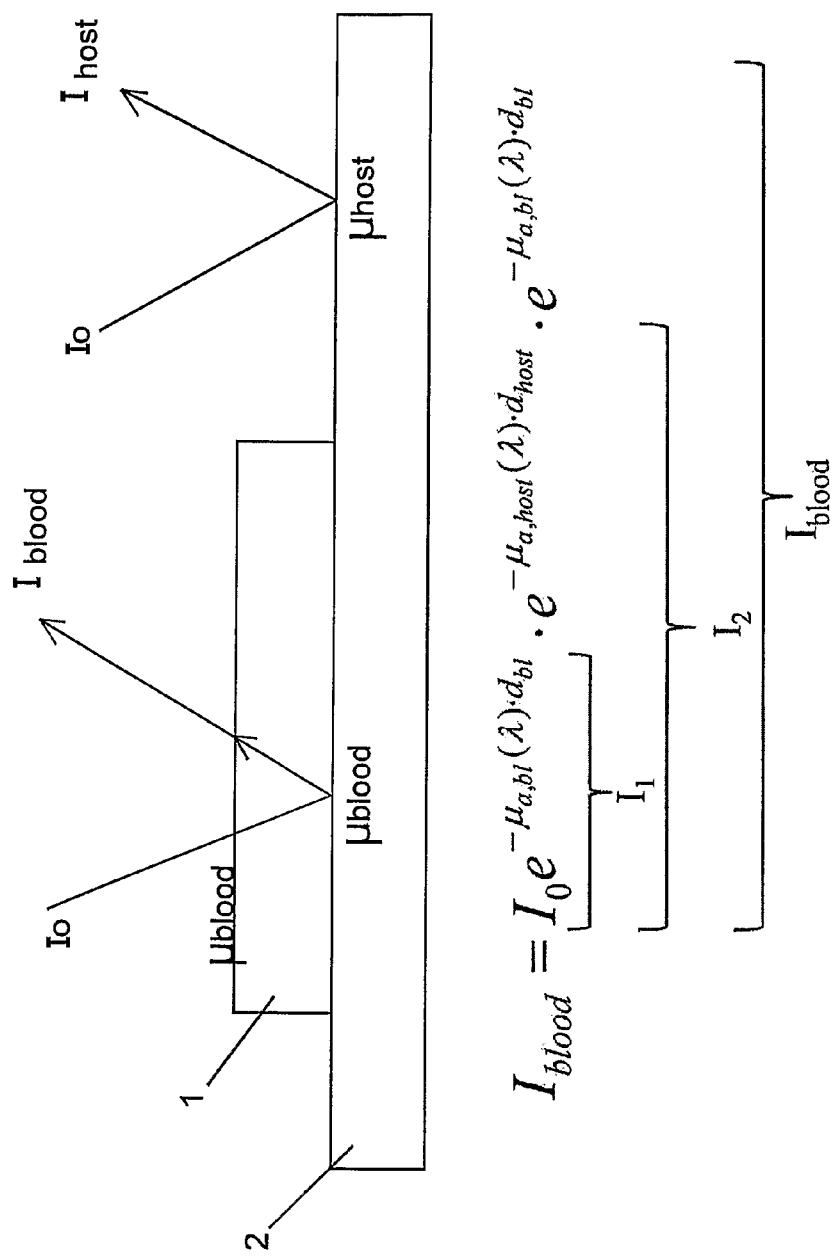
FIG. 6 is a schematic diagram of the geometry of a simple model of light reflectance from two layers.

Similarly, for the bloodstain, the light detected is dependent on the incident light and on the absorbance of the bloodstain. This is illustrated schematically in FIG. 6, where the geometry of the situation, is shown in simplified form considering a simple model of two layers, being the blood stain 1 and the host material 2. As will be apparent, the intensity of the light detected at the detector $I_{blood}$, whether it be the spectrograph 7, the photodetector 16 or the Spectral Imaging Camera 24, at a particular wavelength, will depend on the intensity of the incident light $I_0$ directed onto the bloodstain and will depend on the amount of light reflected by the bloodstain, reflected by the host material and then transmitted by the bloodstain. This can be expressed, simply as:

$$I_{blood} = I_0 e^{-\mu_{a,bl}(\lambda) \cdot dbl} \cdot e^{-\mu_{a,host}(\lambda) \cdot dhost} \cdot e^{-\mu_{a,bl}(\lambda) \cdot dbl}$$

where $I_{blood}$ is the intensity of the received light;

$I_0$ is the intensity of the incident light;

$\mu_{a,host}(\lambda)$ is the absorption coefficient of the host material (in mm$^{-1}$) at wavelength $\lambda$; and $\mu_{a,bl}(\lambda)$ is the absorption coefficient of the bloodstain (in mm$^{-1}$) at wavelength $\lambda$;

$d_{host}$ is the optical pathlength through the host (in mm); and $d_{bl}$ is the optical pathlength through the bloodstain (in mm).

Rearranging this equation provides:

$$I_{blood} = I_0 e^{-\mu_{a,host}(\lambda) \cdot dhost} \cdot e^{-\mu_{a,bl}(\lambda) \cdot dbl} \cdot e^{-\mu_{a,bl}(\lambda) \cdot dbl}$$

and inserting the above equation for $I_{host}$ into this equation gives:

$$I_{blood} = I_{host}^{-\mu_{a,bl}(\lambda) \cdot dbl} \cdot e^{-\mu_{a,bl}(\lambda) \cdot dbl}$$

which can be simplified to:

$$I_{blood} = I_{host}^{-2\mu_{a,bl}(\lambda) \cdot dbl}$$

and which can, in turn be rearranged to give:

$$\mu_{a,bl}(\lambda) \cdot x_{bl} = -2 \ln \frac{I_{blood}}{I_{host}}$$

showing how the ratios of the received light from the bloodstain and the host material at different wavelengths provide the absorbances at each wavelength giving an absorbance spectrum.

Figure 7:
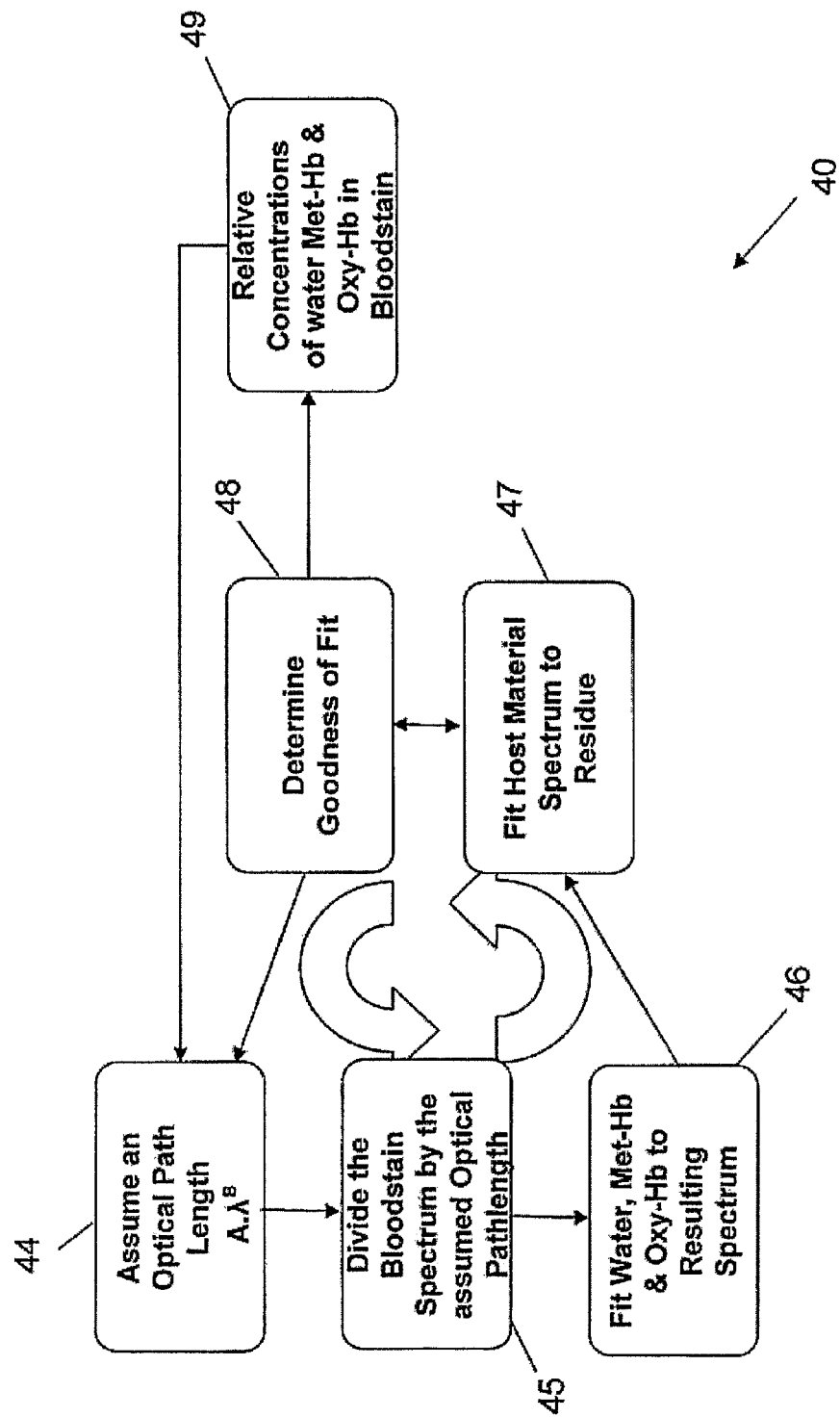
FIG. 7 is a schematic flowchart of the process for determining concentrations of metHb & oxyHb in the process of FIG. 5.

Thus, once the absorbance spectra of the bloodstain and the host material are determined, they can be used, together with the known spectra of blood, oxy-haemoglobin, met-haemoglobin and water as the input matrix for the fitting procedure to determine the relative concentrations of met-haemoglobin and oxy-haemoglobin in the bloodstain (40). One example of a process that can be used to make this determination (40) is shown in more detail in FIG. 7. In this process, a slope is guessed 44 which must account for the wavelength dependent, pathlength in the medium. In practice this will be an offset with a small slope. A first guess is made of the wavelength dependent pathlength in the medium. This is later optimized to the value which gives the best fit. In the MIE scattering regime, where the size of the scattering particles is of the same order as the wavelength, the scattering can be described as a function of wavelength as A*lambda$^B$, where:

A is a scale factor, dependent on the density of the scatterers in the medium; and B is the slope which depends on the size of the particles.

Then, the measured absorbance spectrum is divided by this slope (45) to provide a corrected spectrum and the known spectra of oxy-haemoglobin and met-haemoglobin are fitted (46) using a linear constrained optimisation fitting algorithm to the corrected spectrum. The known spectrum (as previously determined) of the host material is then fitted (47) to the residue. The concentrations of the met-haemoglobin and oxy-haemoglobin are thus determined and the final residue is calculated. The known residue is used to determine how good the fit is (48); when the residue is at a minimum, the fit is as good as it can be. At this point, the concentration of oxy-haemoglobin and met-haemoglobin are stored (49) and the same process is carried out for the measurements at the next time point. Measurements are also carried out at different positions on the bloodstain to see whether the bloodstain is homogeneous, or whether there is a variation within a stain and what the variation is.

Figure 8:
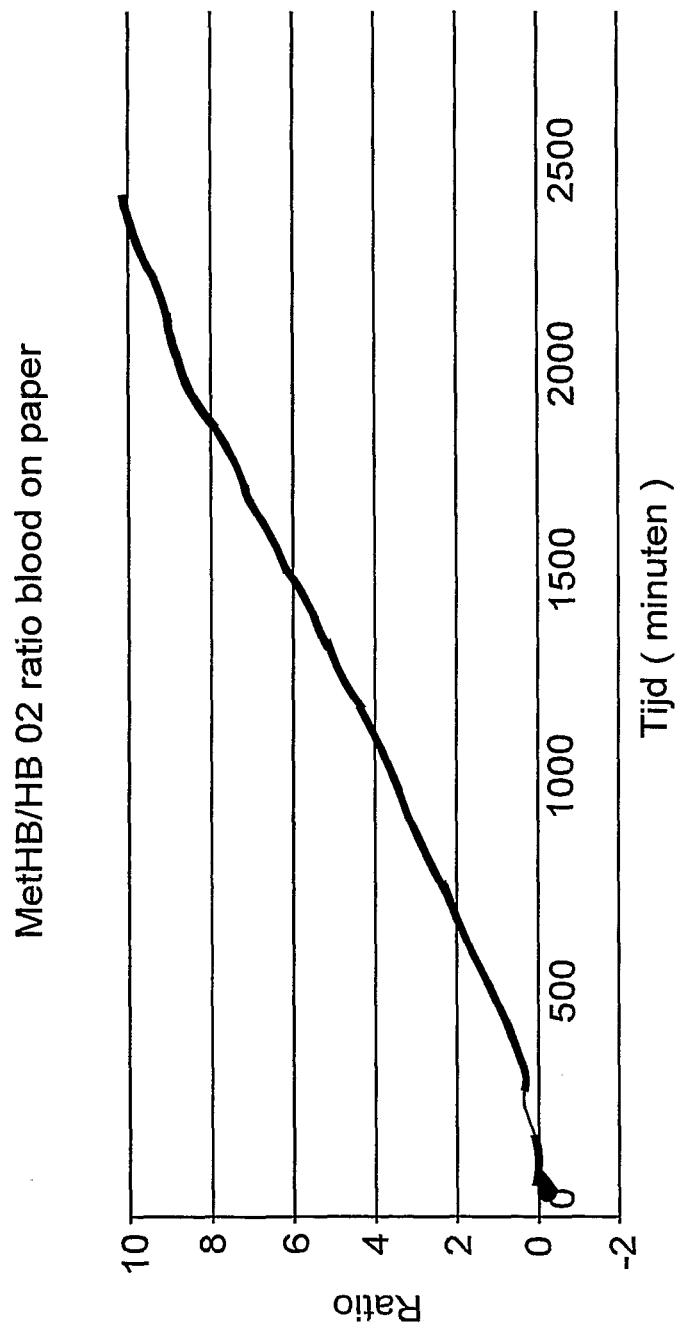
FIG. 8 is a schematic graph showing the change of the ratio of the concentrations of metHb & oxyHb over time in a bloodstain on paper.

Referring back to FIG. 5, once the relative concentrations of met-haemoglobin and oxy-haemoglobin in the bloodstain have been determined, their ratio at each point in time can, of course, easily be calculated (41). These ratios at different times are then plotted against time to determine the rate of change of the ratio (42). The rate of change of this ratio provides an indication of the rate at which the oxy-haemoglobin is converted to met-haemoglobin. By extrapolating this back in time to a point at which there was no met-haemoglobin provides the time (43) at which the blood was first exposed to the air, i.e. when it was first spilt. Examples of the changes in the ratios of met-haemoglobin to wry-haemoglobin over time are shown in FIGS. 8 and 9, where the results are for bloodstains on different host materials, i.e. for a bloodstain on paper (FIG. 8) and for a bloodstain on wood (FIG. 9).

Figure 9:
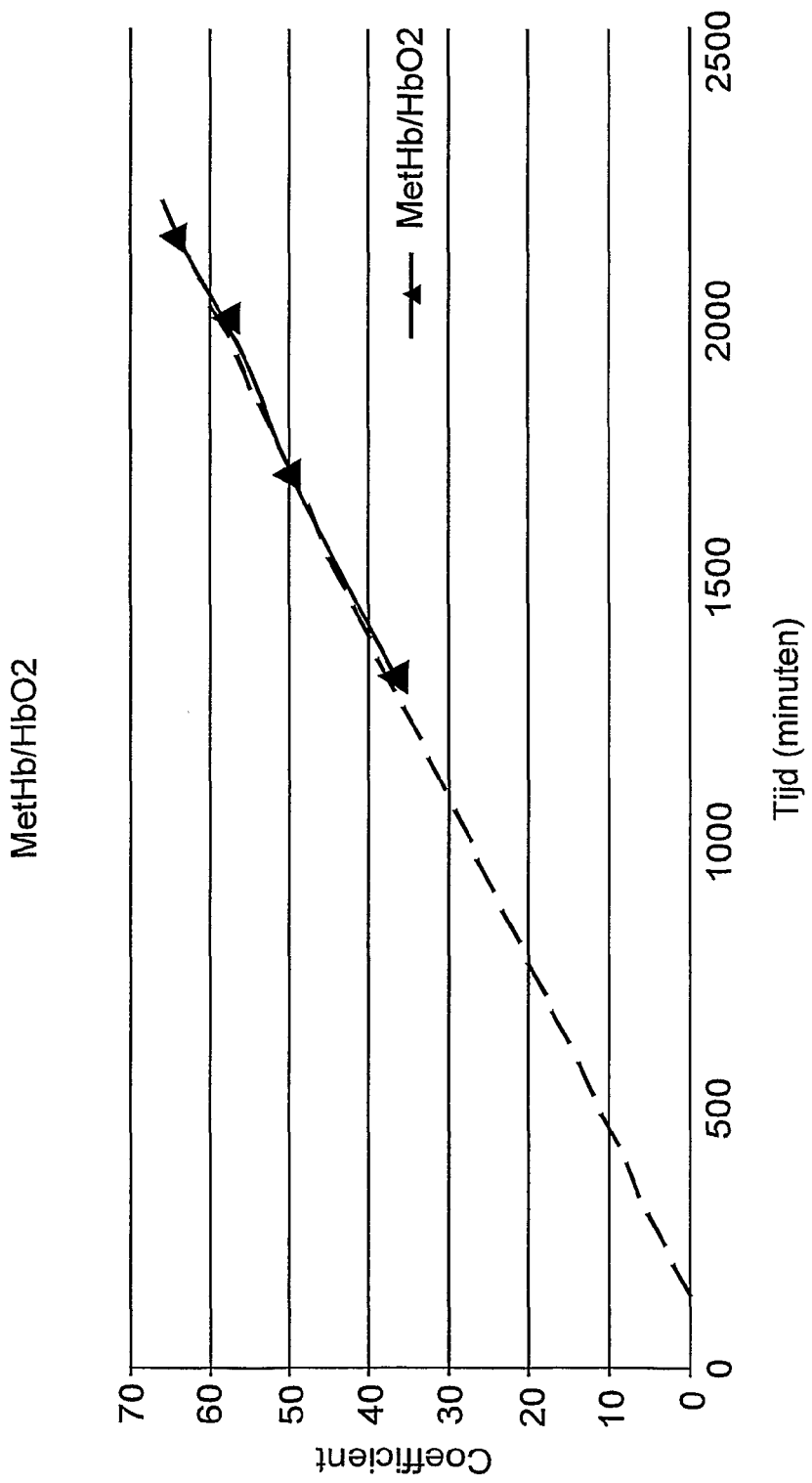
FIG. 9 is a schematic graph showing the change of the ratio of the concentrations of metHb & oxyHb over time in a bloodstain on wood.
Figure 10:
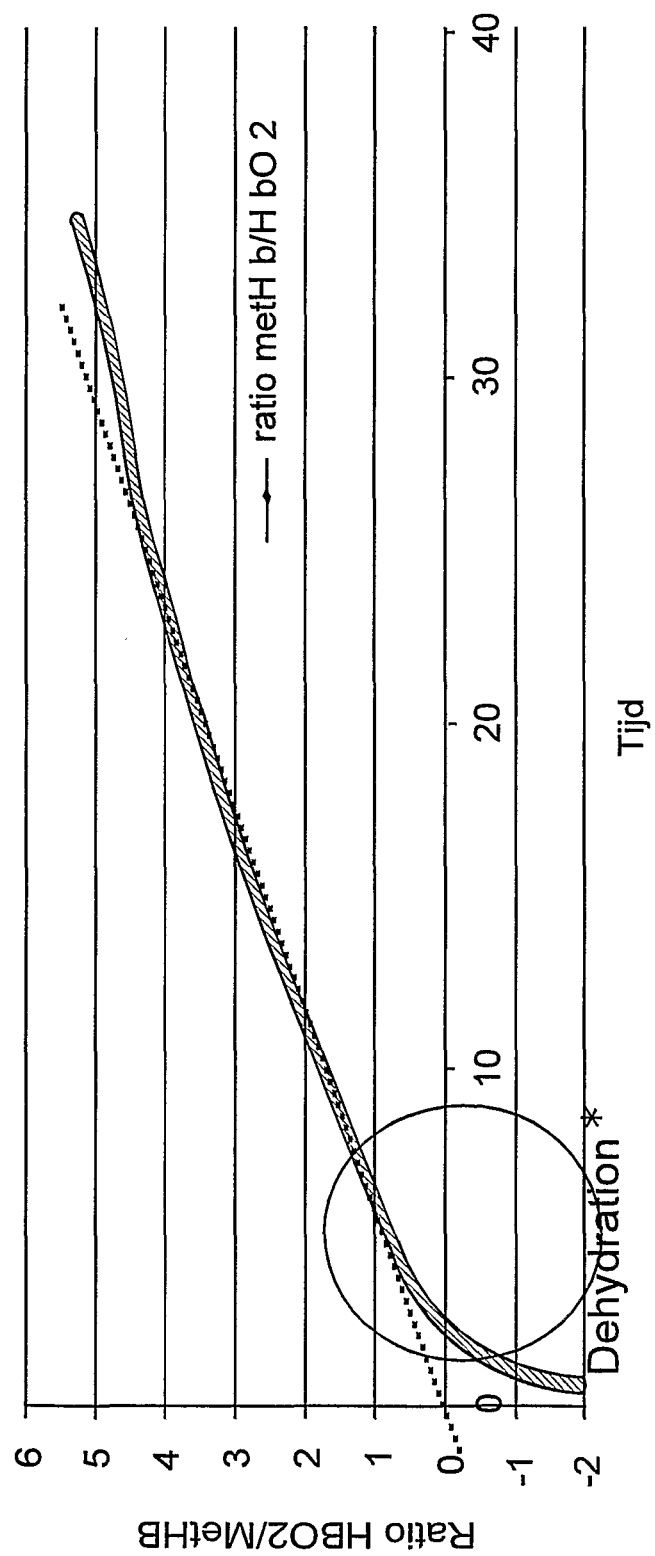
FIG. 10 is a schematic graph showing the change of the ratio of the concentrations of metHb & oxyHb over time in a bloodstain on cloth.

FIG. 10 shows a similar plot to those of FIGS. 9 and 10, but with cloth as the host material. In this case, it will be seen that the beginning of the plot shows a steep fall towards zero time. This is because of the dehydration that occurs. It is reported that an average dehydration time is about two hours, depending, of course, on the host material, temperature, and humidity. As can be seen, using the present technique, the straight line extrapolation of the line provides a time zero (since this was known). However, when such a dehydrated bloodstain was analysed using previous techniques, it would give negative results (as compared to the known time zero here), indicating that earlier techniques estimated earlier times for when the blood was spilt than may actually have been the fact. In some cases, an input spectrum for water may also be used to provide the extra information needed to explain the changes from dehydration.

It will, of course, be appreciated that although the technique described above used reflectance spectroscopy, any appropriate type of spectroscopy, such as Raman or reflectance spectroscopy could be used.

Although the above detailed description refers to the inventive technique being applied specifically to dating of bloodstains outside the human body, it can be extended to date bruises, i.e. blood spilt but remaining within the body. In this case, different substances whose concentrations vary with time should be used. For example, although oxy-haemoglobin and met-haemoglobin may no longer be useful substances (since, although there is conversion to met-haemoglobin in the body, this process is regulated with met-haemoglobin reductase, so that there is very little met-haemoglobin in the blood), as mentioned above, haemoglobin and bilirubin can now be used. The same technique can be used, in general, as for oxy-haemoglobin and met-haemoglobin. However, because a bruise includes spreading of blood in three dimensions, rather than just in two as in a bloodstain, it is preferable to carry out the reflectance spectrum measurements not just at different positions across the area of the bruise as seen from outside the body, but also at different depths. This will help to date the bruising and also to try to distinguish two or more bruises that may be present in the same or overlapping position.

Figure 11:
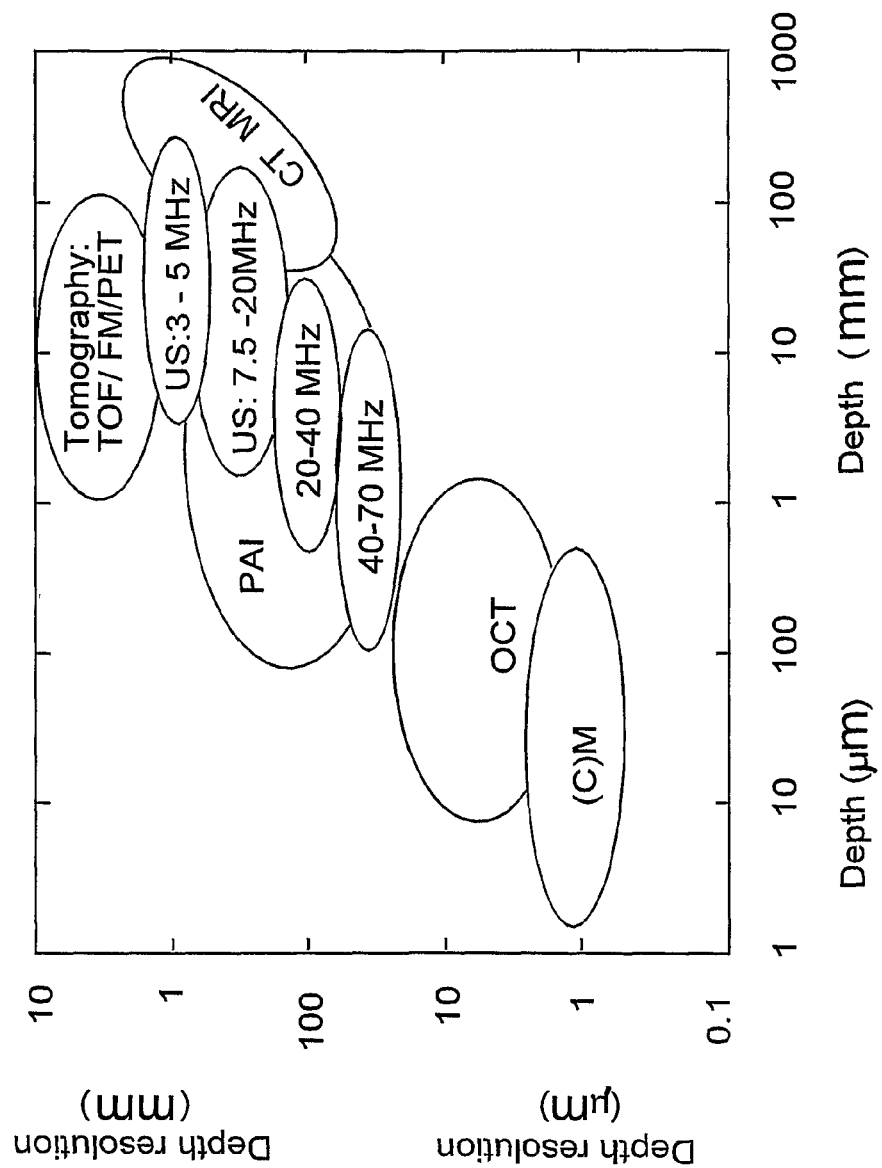
FIG. 11 shows a schematic diagram of imaging depth versus imaging axial resolution for different (functional) imaging techniques.

Most imaging techniques are a trade-off between imaging depth and imaging resolution (see FIG. 11). The high-resolution techniques, (Confocal) Microscopy (CM) and Optical Coherence Tomography (OCT), can be found at the bottom-left corner. CM is capable of visualizing cell layers at micrometer resolution at the cost of a limited penetration depth of 200-400 µm. Typical (axial) resolutions for clinical OCT range from 3 to 20 µm with penetration depths up to 1 mm. Besides anatomical imaging, several extensions of OCT have been developed for functional imaging of tissue physiology, e.g., Doppler OCT for assessment of blood flow and spectral OCT for assessment of tissue oxygenation.

Ultrasound imaging (US) and Photo Acoustic Imaging (PAI) are capable of visualizing structures in the deeper layers. Again, a trade-off has to be made between resolution and imaging depth. With the currently used acoustic frequencies, penetration depth ranges from 0.1 cm up to 10 cm with resolutions from 0.03 mm to 1 mm. Blood flow and changes in reflectivity, e.g., caused by changes in viability, can be visualized with US. However, US is not capable of extracting spectroscopic information hence cannot assess e.g. oxygenation. PAI is capable of measuring spectroscopically but both US and PAI always require contact with the tissue.

At the top right corner, imaging techniques such as Positron Emission Tomography (PET), CT and MRI can be found. Their large penetration depth is achieved at the expense of the limited spatial resolution (0.5 to 3 mm). Functional MRI is based on the increase in blood flow to the local vasculature, e.g. which accompanies neural activity in the brain. PET is a non-invasive functional imaging technique that permits the measurement of biological processes in the living human brain. Using radiotracers which bind to specific receptor sites, PET can quantify the concentration of these receptors which are unoccupied.

Currently, no optical techniques are available for high resolution, depth resolved assessment of spectroscopic information from depths between 1 and 5 mm despite the fact that at this depth range vital structures are located. One of the (clinically) most relevant is the microcirculation, which can provide insight in the systemic as well as the local function of organs.

In order to make the measurements at different depths, two different techniques can be used; one is to use coherent broad band spectroscopy combined with interferometry. The second approach uses non-coherent photon migration measurements to provide input for theoretical light transport models. These can provide depth resolved images of specific tissue chromophores. Combining spatiotemporal spectral information with dedicated algorithms for blood diffusion and blood-bilirubin conversion, allows for a much more accurate determination of the bruise's age.

These techniques utilize spectroscopic analysis of remitted light emanating from tissue in response to a spectrum of incident light (In practice, the signal consists of direct reflected light from the tissue surface and light escaping the tissue from deeper layers. In general in the prior art, the terms reflection, remittance and backscattering are used interchangeably. As these techniques involve imaging as well as depth resolved spectroscopy, they allow functional imaging of diseased tissue. One implementation involves the use of a spectral imaging camera which was developed in cooperation with the physics group of Prof M. Whelan at the Institute for Health and Consumer Protection of the JRC (Joint Research Centre, ISPRA, Italy) and disclosed in "Advanced fluorescence imaging endoscopy using an acousto-optic tuneable filter" by M. P. Whelan, M. Bouhifd, M. Aprahamian, in High-Power Laser Ablation V. edited by Phipps, Claude R. in Proceedings of SPIE, 5486, 295-306, 2004. With this camera, several technical approaches are possible for spatially resolved extraction of physiologically relevant parameters (like blood and tissue oxygenation and the presence of blood components like bilirubin). An alternative uses a fibre based technique for local depth resolved measurements of functional parameters. This is similar to the technique described above in relation to FIG. 1. In this case, however, the fibre ends are placed in direct contact with the skin.

One method of utilising the first technique involves a mode of imaging which may be termed "Scanning Source Imaging". When light is focused on a small spot on the tissue, the 'centre' pixels collect the direct reflected light and the very low order back-scattered light. Light which escapes the tissue further from the entry point will have longer path lengths and is likely to have experienced more scattering events. This creates a diffuse field at longer distances from the source. In this camera, groups of pixels can be selected to measure reflectance at different distances from the entrance point of illumination enabling measurements in the different scattering regimes.

Figure 12:
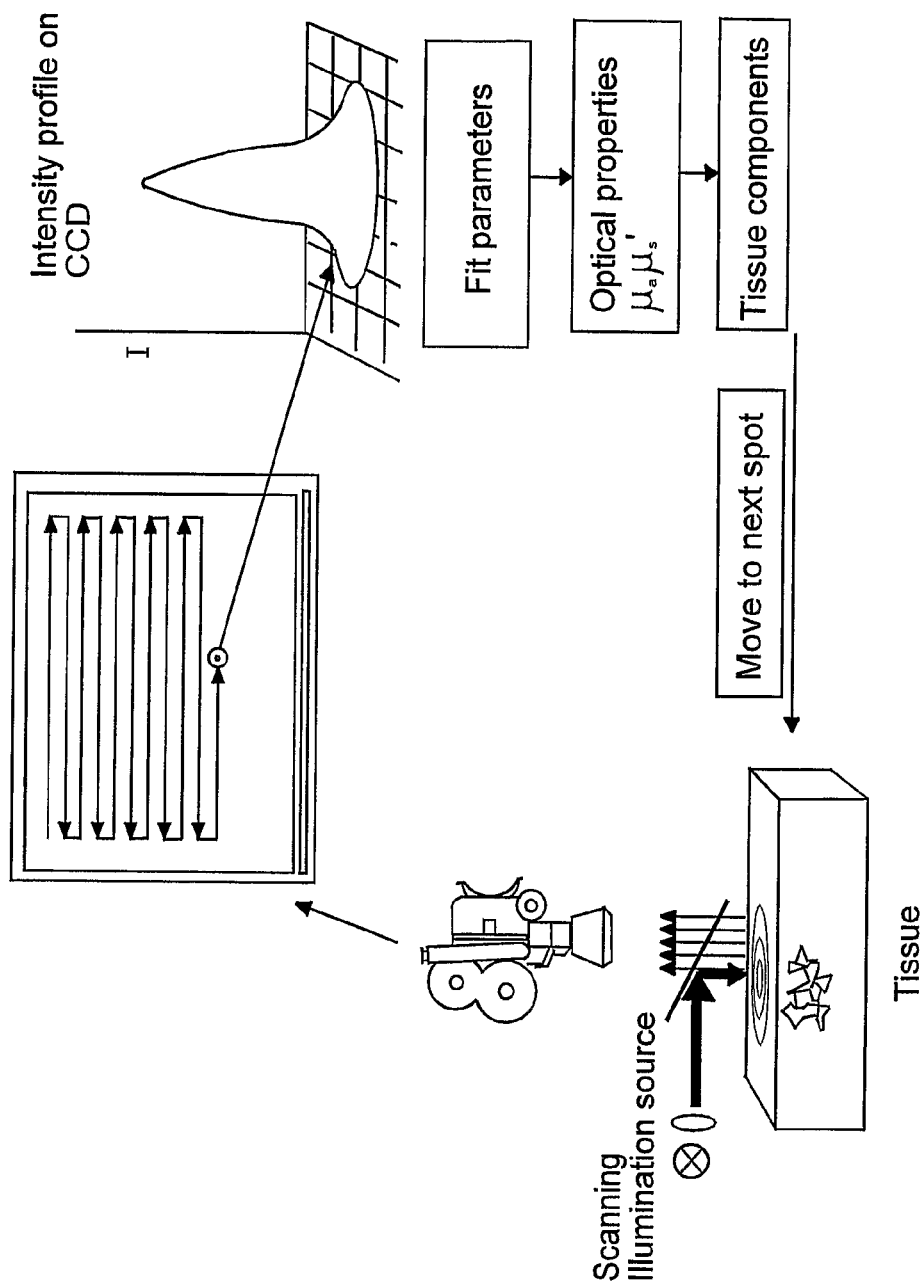
FIG. 12 shows a measurement scheme for scanning point source imaging.

FIG. 12 shows the setup and measurement scheme. By scanning the light spot over the whole target area, an image can be built up from point measurements. The fact that spatially resolved reflectance contains information about the tissue optical properties is used in conventional fibre based diffuse reflectance spectroscopy, where one fibre is used as source fibre and several other fibres to collect the light at several distances from the source fibre. Usually, in spatial resolved measurements, large source-detector fibre distances are used to ensure a diffuse field. This is necessary when for extraction of the optical properties the diffusion approximations (approximate solutions of the light-transport equation) are used. In an article entitled "Time Resolved Reflectance and Transmittance for the Non-Invasive Measurement of Tissue Properties" published in Applied Optics, 28, pages 2231-2336, 1989, by M. Patterson, B. Chance and B. Wilson, there is derived a formula with a semi infinite, half space geometry for a input δ-function, giving the following expression for reflected intensity, R(ρ, t):

$$R(\rho, t) = (4\pi D c_t)^{-\frac{3}{2}} \frac{1}{\mu_s'} t^{-\frac{5}{2}} e^{-\mu_a c_t t} e^{-\left(\frac{\rho^2 + (\mu_s')^2}{4 D c_t t}\right)}$$

where $$D = \frac{1}{3(\mu_a + (1-g)\mu_{tr})}$$

is the diffusion coefficient, $\mu_a$ is the absorption coefficient (cm$^{-1}$), ρ the distance and $\mu_{tr}=\mu_s'=(1-g)\mu_s$ with g, the anisotropy factor=the average cosine of the scattering angle and $\mu_s$=the scattering coefficient. The approximation $\mu_a+\mu_s'\approx\mu_s'$ has been shown to give the following relation:

$$\mu_a \mu_s' \approx \frac{1}{3}\left(\frac{\partial A}{\partial \rho} - \frac{2}{\rho}\right)$$

where the absorbance $$A = \log \frac{I}{I_0}.$$

Thus, by taking the ratio of the ingoing ($I_0$) and remitted (I) intensity as function of distance (pixel number times pixel size, in our case), the product $\mu_a\mu_s'$ can be determined. The wavelength dependence of $\mu_s'$ is then used in a first fit to the total remittance spectrum. The spectral shape of $\mu_a$ can now be obtained using the gradient of attenuation with distance. This is just one solution (approximation) of the transport equation. Other approaches that are known include the δ-E(3) diffusion model, which incorporates the so-called delta-Eddington approximation in order to improve the description of the light transport at shallow depths where standard diffusion theory is of limited accuracy.

The low order scattering regime can be explored using a technique called differential path length spectroscopy (DPS), which can be adjusted for imaging. DPS is known from, for example, a paper entitled "Measurement of the local optical properties of turbid media by differential path-length spectroscopy" by Amelink A, Sterenborg H J. Published in Appl. Opt. 2004 May 20; 43(15):3048-54, and from "Controlling the optical path length in turbid media using differential path-length spectroscopy: fiber diameter dependence" by Kaspers O P, Sterenborg H J, Amelink A. published in Appl. Opt. 2008 Jan. 20; 47(3):365-71. DPS works with the low order scattered light regime close to the source. DPS is sensitive to the optical properties in the most superficial layer of tissue by subtracting the signal measured at a small distance from the source from the direct reflectance (using the delivering fibre for collection). In vivo and ex-vivo experiments have showed that the apparent differential path length is independent of the optical properties of the tissue and depends on the fibre diameter only. As a consequence, the depth of tissue probed by the instrument is small and depends on only the diameter of the probe fibres. The advantage of using the CCD camera is that the amount of pixels can be dynamically changed, which changes the detector surface as well as consequently the probing depth. By using this technique it may be possible, for the first time, to do depth resolved quantitative imaging.

Low Coherence Spectroscopy (LCS), combines optical spectroscopy with optical coherence interferometry. This combination allows the determination of the path length of the backscattered light. By measuring backscattered light from two known depths in the tissue (i.e., the path length is exactly known), the spectrum of the attenuation coefficient of the tissue chromophores can be determined using the Lambert-Beer equation. Because the absorption of the tissue chromophores is known, the composition of the tissue can be obtained e.g. by applying a multiple component fit to the attenuation spectrum. Depending on the focussing optics of the light, measurements can be made within a specific layer in the tissue (e.g. capillary bed, dermis, blood vessels, etc).

As mentioned above, bruising occurs when mechanical force is applied to a person's skin to such a degree that capillaries disrupt, resulting in the leakage of blood into the subcutaneous tissue, the amount of blood, the size and location of the involved area and the time after inflicting the injury accounting for the colour of the bruise. Recently, a mathematical model for the diffusion of blood in the tissue and the conversion to bilirubin has been developed. It describes the extravascular transport of haemoglobin in tissue by the use of Darcy's model for convective flow in porous media and Fick's law for diffusion:

$$j_i = -D_{ik}\frac{\partial N}{\partial x_k} - \xi K_{ik}\frac{\partial p}{\partial x_k}$$

where $j_i$ is the component of the haemoglobin flux vector, $D_{ik}$ is the haemoglobin diffusivity tensor, $K_{ik}$ is the Darcy constant for whole blood (hydraulic conductivity tensor), N is the density of molecular haemoglobin and ξ is the volume fraction of haemoglobin in whole blood. As passive diffusion is the dominant mechanism, the continuity of haemoglobin in a medium with loss can be expressed as:

$$\nabla \cdot \vec{j}_H = -\frac{\partial N_H}{\partial t} - \frac{N_H}{\tau_H}$$

with the haemoglobin releaxation time $$(\tau_H): \frac{1}{\tau_H} = \frac{1}{\tau_L} + \frac{1}{\tau_B} + \frac{1}{\tau_M} + \ldots ,$$

the sum of relaxation times due to lymphatic drainage ($\tau_L$), conversion to biliverdin/bilirubin($\tau_B$) and to macrophage activity($\tau_M$), respectively. For bilirubin, comparable equations apply. As mentioned above, there are several unknown variables in the model, i.e. the various relaxation times, but also the dermal thickness, which may even be the most important parameter here. Thus, the quality of the predictions by the model will be significantly enhanced if a reliable measure of skin thickness can be collected concurrent with the reflection measurement and if reliable estimates of the various time constants become available. By mapping the whole volume of the hematoma, information will be provided about the blood diffusion kinetics likely, allowing assessment of the parameters in the blood diffusion equations and the time constants with more precision than currently available. Therefore, by performing depth resolved quantitative spectroscopic mapping of the bruises, the model's accuracy can be greatly improved, hence, also the determination of the age of the bruises.

Another potential use of the technique is in monitoring of preterm babies. Preterm birth often results in significant neonatal morbidity and mortality due to the immaturity of several organ systems. These systems, e.g. the lungs and vital metabolic systems have to develop to a level of maturity whereby bodily chemical balance has been achieved. Therefore, optimal management of a neonate requires accurate monitoring of multiple functional parameters, e.g. blood oxygenation and bilirubin levels. Currently, functional parameters are monitored offline, which requires frequent lancing of the heel ('heel prick') or venipuncture, both invasive, painful and stressful procedures, to obtain a small volume of blood for laboratory evaluation, up to 5 times a day. Although this sampling frequency is high for the neonate, it is low for the neonatologist and inevitably prolongs the time between onset and detection of a problem, which is unfavourable for optimal management. The primary targets for this clinical application are blood oxygenation and bilirubin concentration. Bilirubin, a breakdown product of heme, comes from degradation of erythrocytes and from other heme pigments. Hyperbilirubinemia (too much bilirubin in the blood) is an increased serum bilirubin level, characterized by jaundice (a yellowish skin colour). Bilirubin is toxic and has to be cleared by the liver. Too high levels may lead to serious brain damage. Observation by the neonatologist is the first method for diagnosis, which often has limited clinical value because neonatal jaundice is rarely perceptible and depends heavily on the experience of the observer. The back up method, the 'heel pricks' are usually accompanied by pulse oximetry. These devices have also disadvantages, i.e., the measurement depends on an adequate arterial pulse and peripheral circulation, implying that in situations such as poor perfusion or shock, the oximeter may not function accurately and, secondly, the poor correlation of oximetry with lower oxygen saturation values. Thirdly, there is no correction of oxygen saturation for abnormal haemoglobin (such as methaemoglobin). The present technique will be able to measure the bilirubin levels and blood oxygenation in the skin of neonates continuously and non-invasively.

Of course, although these techniques only deal with the upper layer of organs (<5 mm), this includes not only the skin, the target organ for dating bruises, but also the organs that can be reached through the body's natural openings, as well as the organs that can be reached endoscopically. These upper layers contain anatomical, vascular and cellular structures that carry information of local but often also of systemic functioning of the patient. An example is the microcirculation that reflects the local status of the organ but in many cases, e.g. for patients in shock, also the systemic problem. Interestingly, systemic problems often show up first as local abnormalities, e.g., complications of cardiac surgery first show up as abnormalities in the oxygen delivery by the microcirculation. In other cases, the blood oxygen saturation level in the microcirculation contains information about the viability of the local circulation and tissue. In addition, information at the local, cellular level is carried by the configuration and concentration of the cytochromes. The so-called functional chromophores (Hb, bilirubin, cytochromes, etc) all have specific absorbing properties for light which makes them particularly attractive targets for optical spectroscopy.

High resolution depth resolved functional information is highly relevant, either for a more precise diagnosis of the problem or for choosing optimal therapy. Examples are: the depth of skin necrosis of a burn wound that determines whether debridement can be performed; the depth distribution of ectatic venules in portwine stains that, when known, might improve laser therapy (better choice of wavelength, pulse duration); the temporal and spatial distribution of haemoglobin, bilirubin and other chromophores that determine the colour of a bruise on the skin due to child abuse or torturing in forensic medicine; oxygenation of the various retinal layers in ophthalmology; splanchnic blood flow and oxygen transport during cardiac surgery, etc. To date, imaging technology that can assess depth resolved performance of tissue with 0.02 mm or less resolution up to 5 mm is not available. Thus, the technique facilitates the determination of other functional chromophores, e.g. cytochrome aa3, which has an oxygenation dependent absorption curve and is a measure of the viability of the tissue at the cellular level. Possible spin-off applications include brain oxygenation measurements of a fetus during delivery, which is one of the 'holy grails' in obstetrics, monitoring the viability of donor organs (kidney, heart, liver) in a (just) deceased donor for organ transplantation, and discrimination between healthy and pathologic tissue based on differences in optical properties, e.g. in oncology. Also, measurements of functional parameters on structures/organs inside the body are possible when the techniques will be developed for endoscopic use.

In order to carry out the spectroscopic imaging in three dimensions, a similar technique to that described above is used, except that models for the depth of a lesion, the diffusion of blood and the incorporation of haemoglobin into bilirubin are incorporated (in the case of bruise dating). The fitting procedure yields local concentrations of haemoglobin and bilirubin, which are used to determine the parameters for the analytical model described below.

Figure 13:
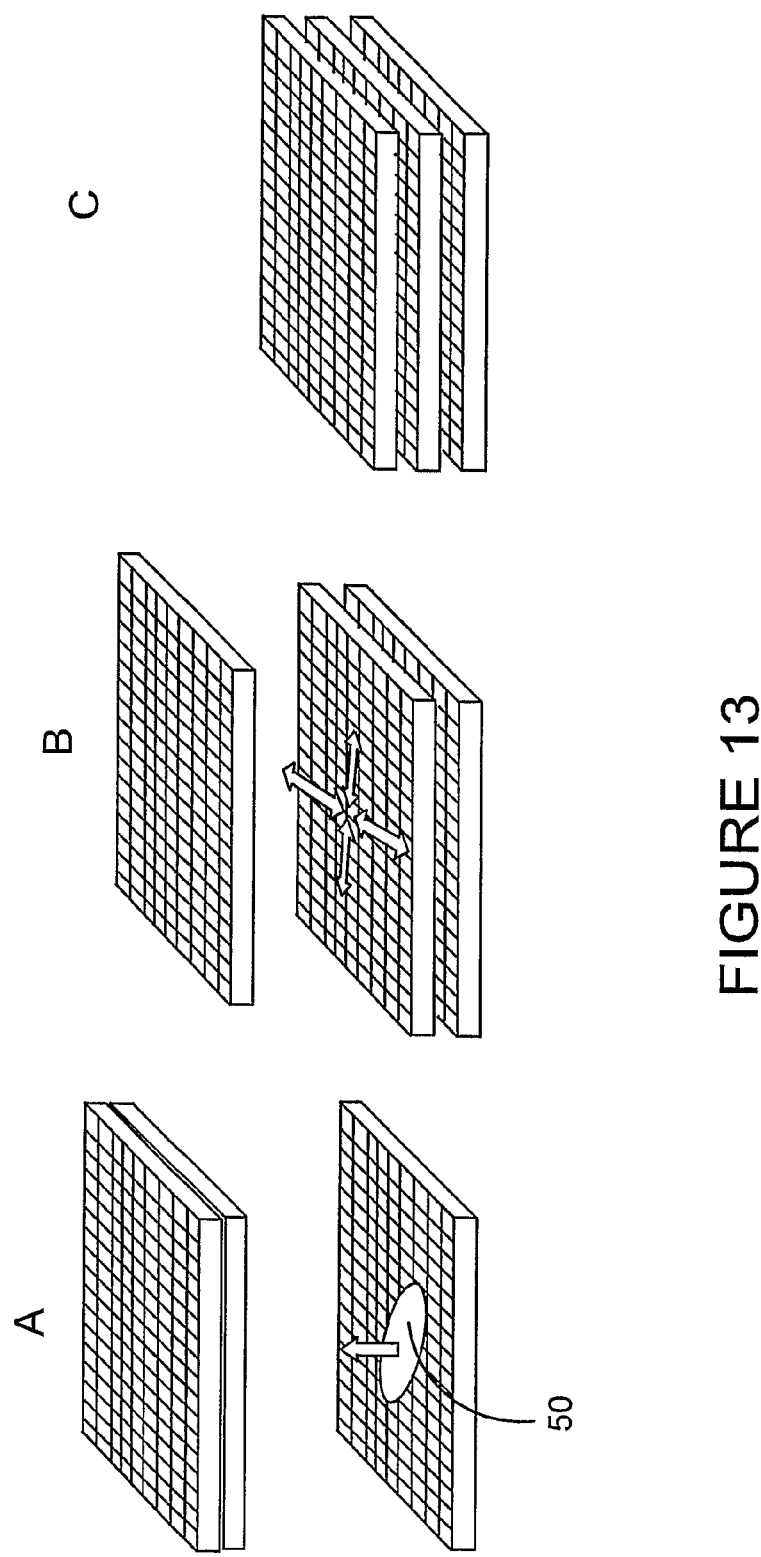
FIG. 13 shows a model used to describe the development and fading of bruises.

In this case, a model is used to describe the development and fading of bruises. The model is set up as a 3D infinite grid with three layers of tissue, as shown in FIG. 13. Each cell in the grid interacts with its neighbouring cells. Haemoglobin can diffuse into and out of the cells depending on the concentrations inside that particular cell and its neighbours. In FIG. 13A, there is shown a large pool of haemoglobin 50 formed in a subcutaneous bottom layer 51, which diffuses into the mid dermal layer 52 by active diffusion following Darcy's Law:

$$j_i = -K_{ik} \frac{\partial p}{\partial x_i},$$

where $j_i$ is the component of the blood flux vector, p is the local pressure, $x_i$ is the spatial coordinate of a Cartesian system and $K_{ik}$ is the hydraulic conductivity tensor. The blood also diffuses passively, following Fick's law:

$$j_i = -D_{ik} \frac{\partial N}{\partial x_k}$$

where $D_{ik}$ is the haemoglobin diffusivity. In the dermal layer 52, there is blood and bilirubin diffusion described by Fick's law, conversion of haemoglobin to bilirubin described by Michaelis Menten kinetics:

$$\frac{d[Hb]}{dt} = -\frac{V_{max} \cdot [Hb]}{Kmm + [Hb]}$$

and clearance of bilirubin, again described by Michaelis Menten kinetics, as shown in FIG. 13B. The parameters in the Michaelis Menten kinetics equation, $V_{max}$ (maximum reaction rate) and $K_{mm}$ (the Michaelis Menten constant, which is a measure of the affinity of the enzymes for the reaction), are used as optimization parameters for fitting the model to the measured data. In this model, as shown in FIG. 13 C, it is assumed that there is no diffusion into the top epidermal layer 53. The fitting process starts by guessing all of the model's parameters (Blood pool size, $D_{ik}$, $K_{ik}$, dermal thickness, $V_{max}$, and $K_{mm}$. The consequences are then calculated and the results (spatially resolved blood and haemoglobin concentrations) are compared to the experimental data. If it disagrees with the experimental data, then the initial guesses are wrong and are adjusted. This continues until the model fits the experimental data. At that stage, the model can be used to calculate the age of the bruise.

Figure 14:
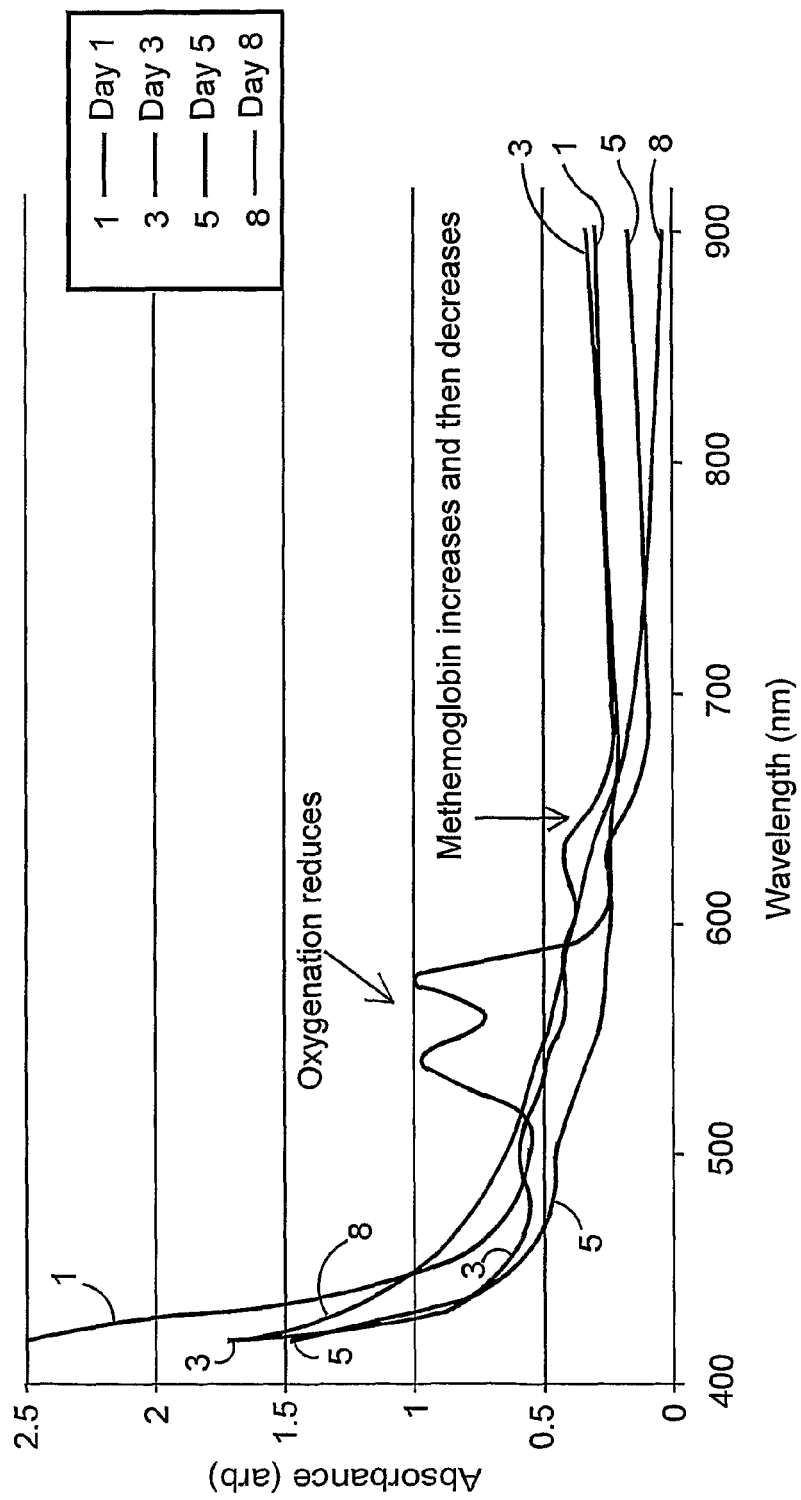
FIG. 14 shows the absorbance spectra measured using the fibre-based apparatus on a Tissue Equivalent Phantom (TEP)

FIG. 14 shows the absorbance spectra measured using the fibre-based apparatus on a Tissue Equivalent Phantom (TEP), which are a mixture of scattering and absorbing materials that together represent the optical properties of tissue, i.e. an artificial construct that is designed to mimic the optical properties of tissue. As can be seen, over the course of several days, the oxygenation of the TEP decreases, while the met-haemoglobin content increases and then decreases. Measurements on actual bruises show very similar results.

Figures 15A, 15B:
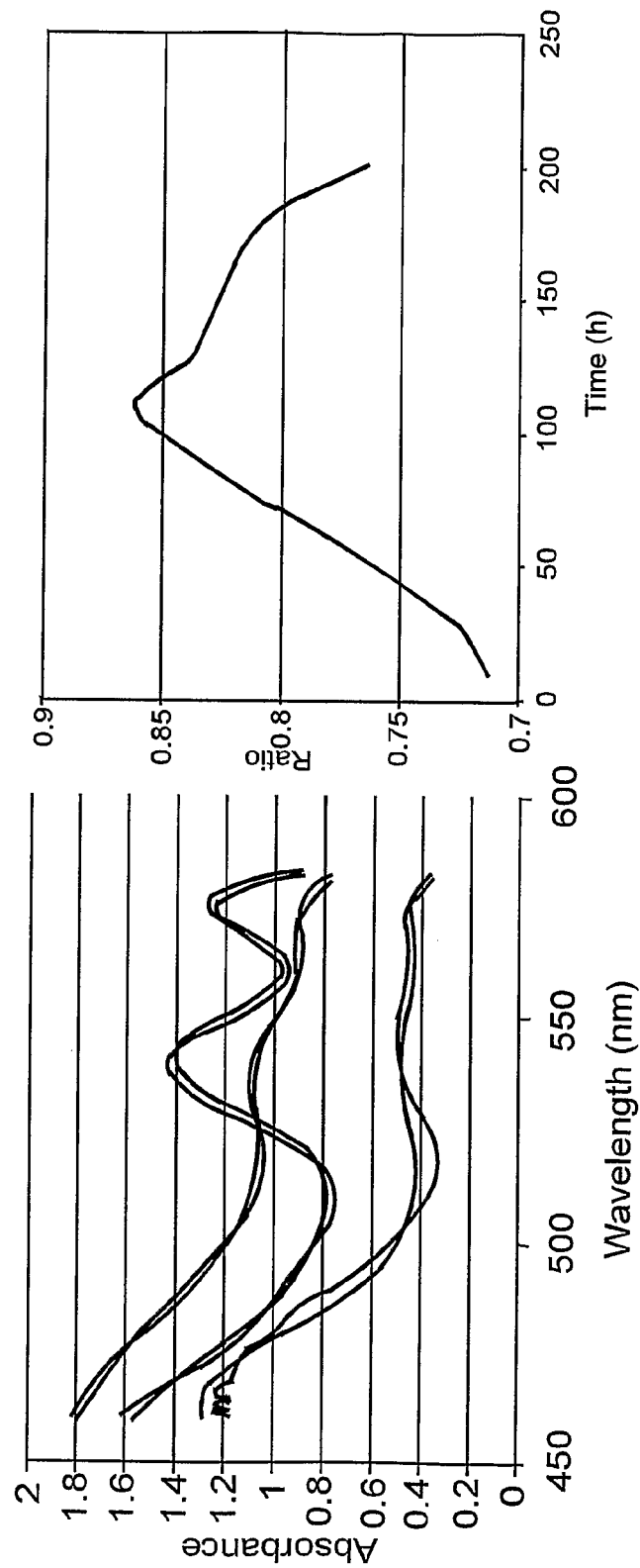
FIG. 15 shows the absorbance curves at three different times and the bilirubin/haemoglobin ratio as a function of time.

From the fitting procedure, relative concentrations are obtained, which are expressed in haemoglobin/bilirubin ratios, as shown, by way of example, in FIG. 15. FIG. 15A shows the absorbance curves at three different times and the fitting results for each one. The fit parameters give the relative concentrations of the chromophores. FIG. 15B shows the bilirubin/haemoglobin ratio as a function of time, measured in the centre of a bruise (in the upper arm of a healthy adult).

Figure 16:
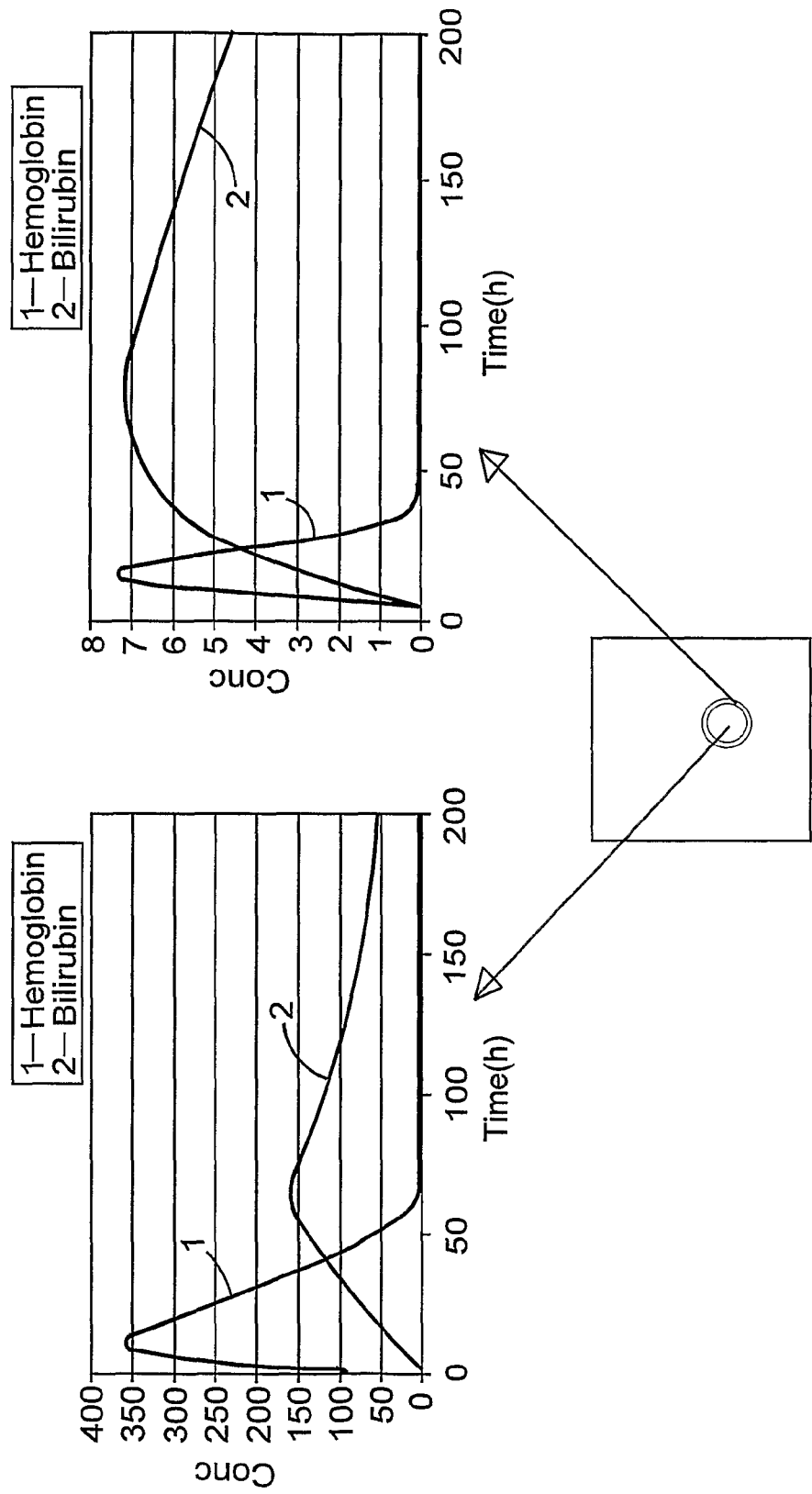
FIG. 16 shows a mathematical model of the dynamics of haemoglobin and bilirubin concentrations as a function of time and position.

The mathematical model provides haemoglobin and bilirubin concentrations as a function of time and position, as shown in FIG. 16, where the left side shows the results of the simulation for the centre of the bruise and the right side shown the simulation results for the edge of the bruise. The calculations of the dynamics of the haemoglobin and bilirubin were carried out for hourly step intervals, where $D_H=1.2\times10^{-11}$ m$^2$/s; dermal thickness=1 mm; $K_{mm}=2$; $V_{max}=10$. These parameters give results that are within the range of measured data.

Thus, the chromophores within a bruise can be identified individually and spatio-temporal dynamics can be assessed using the methods described above. The dynamics can be followed over several days.

It will, of course, be appreciated that the methods described above can also be used for determining the age of a non-fluid body sample, for example, skin. In this case, although, again, any appropriate type of spectroscopy, such as Raman or reflectance spectroscopy could be used, a particularly useful technique would be the use of fluorescence spectroscopy and the two substances could usefully be collagen and cross-linked collagen, which would enable the post-mortal time of the skin sample to be determined.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example microwave or infrared. The series of computer instructions can constitute all or part of the functionality described above, and can also be stored in any memory device, volatile or non-volatile, such as semiconductor, magnetic, optical or other memory device.

It should be appreciated that references to "light" herein refer to electromagnetic radiation of wavelengths between about 300 nm and about 10 μm, preferably between about 400 nm and about 2 μm, and very preferably between about 800 nm and about 1700 nm.

It will be apparent that different appropriate light sources can be used, as desired, according to the particular purpose and wavelengths required. For example, although several different light sources may be present in an apparatus, such as the three LEDs described above, other types and/or numbers of light sources may be present and they may be arranged to be controlled so that only one or a particular combination are turned on at a particular time, with, perhaps, another one or particular combination being turned on at another time, when the first one or combination is switched off. Thus, any appropriate light source(s) can be used and switched on and off with another appropriate light source(s). This is particular useful in the case of fluorescence spectroscopy where one or more excitation light sources may need to be used to excite the sample being analysed.

It will also be appreciated that although only some particular embodiments of the invention have been described in detail, various modifications and improvements can be made by a person skilled in the art without departing from the scope of the present invention as defined by the following claims.

The invention claimed is:

1. A method of dating a body sample comprising:
   taking a spectroscopic measurement of a host material;
   taking a series of spectroscopic measurements of the sample, each measurement in the series of spectroscopic measurements including at least two predetermined positions in a spectrum, the predetermined positions having spectral characteristics corresponding to two predetermined substances present in the sample that have a time varying relationship with each other, the measurements in the series of spectroscopic measurements being spaced in time;
   determining a concentration of each of the two predetermined substances present in the sample from each measurement in the series of the spectroscopic measurements at each point in time;
   determining a ratio of the concentrations of the two predetermined substances at each point in time;
   analyzing the ratios of the concentrations of the two predetermined substances over time to estimate when the concentrations of the two predetermined substances were at a limit of their concentrations, thereby providing an indication of the age of the sample; and
   wherein determining the concentrations of the two predetermined substances from the series of spectroscopic measurements comprises:
      dividing a measured absorbance spectrum obtained from the series of spectroscopic measurements of the sample by an assumed optical path length to provide a corrected absorbance spectrum;
      fitting measured spectra of the two predetermined substances to the corrected absorbance spectrum to obtain a residue, and
      fitting the spectroscopic measurement of the host material to the residue to obtain relative concentrations of the two predetermined substances within the sample.

2. A method of dating a body sample according to claim 1, wherein the sample is either inside or outside the body.

3. A method of dating a body sample according to claim 1, wherein the sample is skin.

4. A method of dating a body sample according to claim 1, wherein the sample is a body fluid.

5. A method of dating a body sample according to claim 4, wherein the body fluid is blood.

6. A method of dating a body sample according to claim 5, wherein one of the two predetermined substances is hemoglobin and the other substance is met-hemoglobin.

7. A method of dating a body sample according to claim 1, wherein the series of spectroscopic measurements comprises reflectance, Raman or fluorescence spectroscopic measurements.

8. A method of dating a body sample according to claim 1, wherein one of the two predetermined substances is hemoglobin and the other of the two predetermined substances is bilirubin.

9. A method of dating a body sample according claim 1, wherein the series of spectroscopic measurements comprise interferometric spectroscopic measurements made at a series of depths in the body.

10. A method of dating a body sample according to claim 1, wherein the series of spectroscopic measurements include measurements made at several different lateral positions on the body.

11. A method of dating a body sample according to claim 1, wherein the series of spectroscopic measurements provide several series of measurements, for each of which an estimate of when the concentrations of the two predetermined substances were at a limit of their concentrations is determined, and the estimates for all the several series are analyzed to provide an indication of the age of the sample.

* * * * *